United States Patent [19]

Hoegnelid et al.

[11] Patent Number: 5,016,632

[45] Date of Patent: May 21, 1991

[54] MEDICAL DEVICE AND METHOD FOR STIMULATING A PHYSIOLOGICAL EVENT IN A PATIENT WITH A STIMULATION INTENSITY AUTOMATICALLY ADAPTING TO THE PHYSICAL ACTIVITY OF THE PATIENT

[75] Inventors: Kurt Hoegnelid, Sundbyberg; Jan Ljungstroem, Solna, both of Sweden

[73] Assignee: Siemens Aktiengesellschaft, Berlin and Munich, Fed. Rep. of Germany

[21] Appl. No.: 572,417

[22] Filed: Aug. 27, 1990

[30] Foreign Application Priority Data

Aug. 28, 1989 [EP] European Pat. Off. ........ 89115849.5

[51] Int. Cl.⁵ .............................................. A61N 1/365
[52] U.S. Cl. .............................................. 128/419 PG
[58] Field of Search .................... 128/419 PG

[56] References Cited

U.S. PATENT DOCUMENTS

| 4,325,384 | 4/1982 | Blaser et al. | 128/419 PG |
| 4,428,378 | 1/1984 | Anderson et al. | 128/419 PG |
| 4,776,338 | 10/1988 | Lekholm et al. | 128/419 PG |
| 4,892,100 | 1/1990 | Schaldach | 128/419 PG |
| 4,926,863 | 5/1990 | Alt | 128/419 PG |
| 4,972,834 | 11/1990 | Beggmann et al. | 128/419 PG |

FOREIGN PATENT DOCUMENTS 3709022 9/1989 Fed. Rep. of Germany .
8701947 4/1987 PCT Int'l Appl. .

*Primary Examiner*—William E. Kamm
*Attorney, Agent, or Firm*—Hill, Van Santen, Steadman & Simpson

[57] ABSTRACT

An implantable medical device for stimulating a physiological event in a patient at a stimulation intensity includes circuitry for adapting the stimulation intensity to the physical activity of the patient with refernce to a parameter contained within a physical activity signal obtained from a sensor. Circuitry is also provided for reducing, under certain circumstances, the sensitivity for the parameter of the physical activity signal which is used to adapt the stimulation intensity. Reducing the sensitivity ensues dependent on the time over which the stimulation intensity is below a defined threshold. A method for operating the device is also disclosed.

9 Claims, 2 Drawing Sheets

MEDICAL DEVICE AND METHOD FOR STIMULATING A PHYSIOLOGICAL EVENT IN A PATIENT WITH A STIMULATION INTENSITY AUTOMATICALLY ADAPTING TO THE PHYSICAL ACTIVITY OF THE PATIENT

BACKGROUND OF THE INVENTION

1. Field of the Invention

The present invention is directed to a medical device implantable in the body of a patient which includes means for stimulating a physiological event in the patient with an adjustable stimulation intensity, and wherein the sensitivity which is used to set the stimulation intensity, with reference to a signal from a sensor, can be reduced, and to a method for operating such a device.

2. Description of the Prior Art

Implantable devices for stimulating a physiological event in a patient with a stimulation intensity which is automatically adapted to the physical activity of the patient are known in the art. Information regarding the physical activity of the patient is obtained from a sensor, usually also implanted in the patient for generating a physical activity signal. The selected parameter of the physical activity signal is then monitored and variations in this parameter cause corresponding adjustments in the stimulation activity. It is also known to lower, under certain circumstances, the sensitivity which is used to set the stimulation intensity with reference to the signal from the sensor.

As used herein, the term "stimulation intensity" means any parameter, or combination of parameters, of the signal which is supplied from the device to the patient to stimulate the desired physiological event. This can include the duration, the frequency, the repetition rate, the amplitude, and combinations thereof, with which the means for stimulating in the device take effect to bring about the stimulation of the event. The term "sensitivity" as used herein indicates the value which the selected parameter of the physical activity signal, which is used as an indicator of the physical activity, must have in order to cause the setting of a specific stimulation intensity. A reduction in the sensitivity thus means that a higher value of the signal parameter, such as amplitude, must be present at a current time than was previously necessary in order to cause a setting of the same stimulation intensity.

Such devices are intended to permit the patient in whom the device is implanted to lead as normal a life as possible. Dependent on the physical activity of the patient, the physiological event should be stimulated with a stimulation intensity which corresponds as closely as possible to that which would be present in a healthy patient, given the same physical activity. This should be guaranteed both for conditions of high physical activity and for resting conditions.

A device of this type is disclosed in European application 0 080 348, corresponding to U.S. Pat. No. 4,428,378. This patent discloses an implantable heart pacemaker having a housing in which a piezoelectric pressure sensor is disposed, the sensor monitoring mechanical oscillations in the patient which arise during physical activity of the patient in whom the pacemaker is implanted due to movements of the muscles and connecting structure which propogate as pressure waves. These mechanical oscillations are then converted by the sensor into a corresponding electrical signal. The stimulation intensity, i.e. the stimulation rate with which the pacemaker stimulates the heart in the absence of natural heart beats, is then set dependent on the physical activity of the patient with reference to this signal. It is possible to reduce the sensitivity with which the adaptation of the stimulation frequency ensues with reference to the signal from the piezoelectric pressure sensor, proceeding from a maximum value. This permits the stimulation intensity to be matched to individual conditions. Adaptation of the stimulation intensity ensues between upper and lower limit values, the upper limit value being reached during conditions of extremely high physical activity, and the lower limit value taking effect in the resting condition, for example, during sleep. A problem in this known device is that during sleep the patient in whom the pacemaker is implanted assumes a position causing pressure to be externally exerted onto the piezoelectric pressure sensor. This causes the sensor to generate a signal without the presence of physical activity on the part of the patient. This in turn causes an increase in the stimulation repetition rate, which is uncomfortable for the sleeping patient.

SUMMARY OF THE INVENTION

It is an object of the present invention to provide an implantable device for stimulating a physiological event in a patient in the manner described above wherein the risk of false increases in the stimulation intensity is reduced during phases wherein the body of the patient in whom the device is implanted is in a rest condition, particularly when the patient is sleeping.

It is a further object of the present invention to provide a method for operating such a device.

The above objects are achieved in an apparatus including the following structure, and operating in the following manner. Means are provided for identifying the stimulation intensity currently being used by the device to stimulate a physiological event. The device also includes means for comparing the stimulation intensity to a threshold, and means for calculating the chronological duration over which the stimulation intensity falls below the threshold. This chronological duration is then compared to a minimum chronological duration. If the minimum chronological duration is upwardly exceeded, the sensitivity is lowered to a sensitivity value lying below the normal value. For example, if the stimulation intensity has dropped over a certain minimum time span, for example 30 minutes, to a value which is slightly above the stimulation intensity present for the resting condition (such as the sleep condition), it is assumed that the patient in whom the device is implanted is in fact in a rest condition, and lowering of the sensitivity to a value below the normal value is undertaken. It is thus assured that signals from the sensor will not result in an undesired increase in the stimulation intensity under these conditions.

In a further embodiment of the invention, the means for comparing the stimulation intensity also compare the existing stimulation intensity to a second threshold, lying below the first threshold. The means for calculating a chronological duration also calculate a second chronological duration during which the stimulation intensity falls below the second threshold. The means for comparing chronological durations also compares the calculated, second chronological duration to a second minimum chronological duration. Lowering of the sensitivity from the sensitivity value obtained from the first comparison, to a second sensitivity value lying below the first sensitivity value, takes place when the second minimum chronological duration is exceeded. This embodiment therefore provides the possibility to follow a first lowering of the sensitivity, which may be undertaken as a "trial run," with a further lowering of the sensitivity to a lower, second sensitivity value after it has been assured that the patient is in fact in a long-lasting condition of rest or sleep, and the physical activity has not again increased.

To insure a uniform operation of the device, in a further embodiment a means for forming an average is provided, which forms the chronological average of the calculated stimulation intensity. In this embodiment, the means for comparing the stimulation intensity compare the average of the stimulation intensity to a threshold for the average, and the means for calculating a chronological duration calculate the duration during which the chronological average of the stimulation intensity falls below the threshold for the average.

In one embodiment of the invention, a piezoelectric pressure sensor in mechanical contact with the both of the patient is provided as the sensor. An important advantage of piezoelectric pressure sensors is to enable the generation of a signal corresponding to the physical activity of a patient in a simple and economic way. This advantage is achieved to its fullest effect by the use of the invention disclosed herein, since the aforementioned significant disadvantage of piezoelectric pressure sensors is thereby avoided.

In one embodiment of the invention, the implantable device is a heart pacemaker, and the means for stimulating a physiological event are means for stimulating heart activity in the patient. In this embodiment, the means for adapting the stimulation intensity to the physical activity of the patient are a means for adapting the stimulation repetition rate to the physical activity of the patient.

DESCRIPTION OF THE PREFERRED EMBODIMENTS

Figure 1:
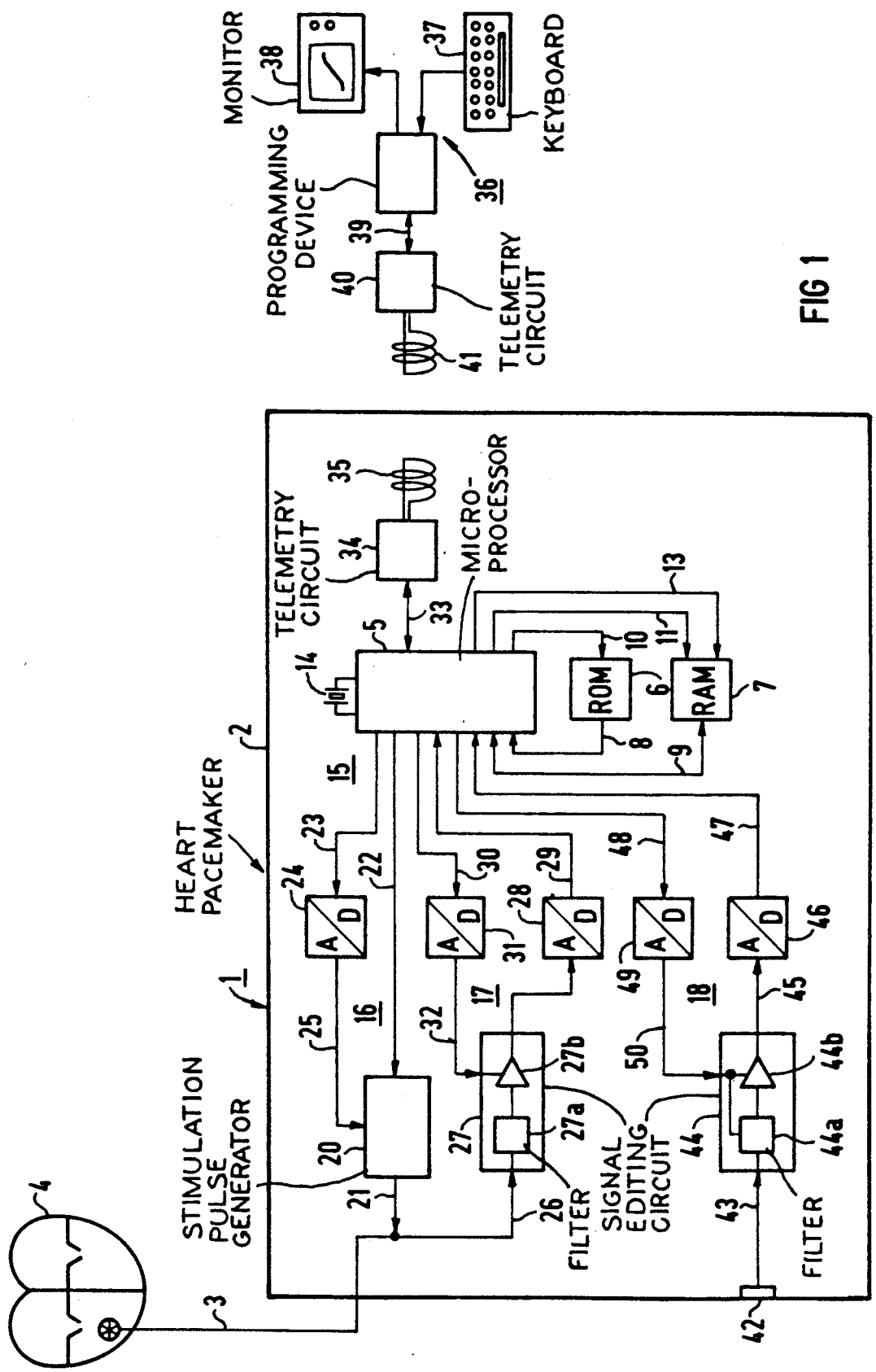
FIG. 1 is a schematic block diagram of a device for stimulating a physiological event in a patient constructed in accordance with the principles of the present invention.

The invention will be explained with reference to FIG. 1 in the embodiment of a heart pacemaker, which is generally referenced at 1. The pacemaker 1 has a schematically indicated housing 2, which is hermetically tight and is suitable for implantation in the body of a patient. An electrode 3 leads from the housing 2 to the heart 4 of a patient, and is attached in a ventricle, preferably the right ventricle, accessible through the vein system. The heart pacemaker 1 is preferably operable in the VVI mode.

Only those components of the pacemaker 1 necessary to explain the invention will be discussed. These include a microprocessor 5, to which a read-only memory (ROM) 6 and a write-read memory (RAM) 7 are connected via respective data lines 8 and 9 and respective address lines 10 and 11. A line 13 for switching the RAM 7 from the write mode to the read mode and vice versa is also connected between the RAM 7 and the microprocessor 5. A program with which all functions of the pacemaker 1 are controlled is stored in the ROM 6. Therefore, when it is stated below that the microprocessor 5 executes a specific function, this is understood to mean that the microprocessor 5 becomes active for the execution of the respective function upon the execution of the program stored in the ROM 6, with utilization of data contained in the RAM 7 and using data supplied to it in some other way, for example, via the other input connections.

A crystal 14, connected to the microprocessor 5, generates the clock signals required for the operation of the microprocessor, and also represents the time reference for the operation of the pacemaker 1.

The microprocessor 5 has input/output connections, generally referenced at 15, which include a plurality of channels 16, 17 and 18.

The channel 16 supplies the heart 4 with stimulation pulses when necessary. The channel 16 therefore includes a stimulation pulse generator 20, having an output line connected to the electrode 3. The stimulation pulse generator 20 can be activated for generating an electrical stimulation pulse via a line 22 connected to a corresponding output of the microprocessor 5. Digital data relating to the shape of the stimulation pulses, for example their amplitude and duration, proceed from the microprocessor 5 via a line 23 to a digital-to-analog interface 24, which supplies the stimulation pulse generator 20 with analog control signals corresponding to the digital data via a control line 25. These control signals set the stimulation pulse generator 20 so that it generates stimulation pulses havinthe desired shape, as needed.

The channel 17 includes a signal editing circuit 27, also connected to the electrode 3 via an input line 26. The signal editing circuit 27 filters and amplifies an electrical signal taken from the heart 4 via the electrode 3 which corresponds to the activity of the heart. The signal editing circuit 27 therefore includes a filter 27a and an amplifier 27b. The edited signal proceeds from the output of the signal editing circuit 27 to an analog-to-digital converter 28. From the converter 28, the digital data proceed via a line 29 to a corresponding input of the microprocessor 5. These digital data correspond to the curve of the electrical signal which is present at the output of the signal editing circuit 27, which in turn reflects the electrical activity of the heart 4. The microprocessor 5 is connected to a digital-to-analog interface 31 via a line 30, which forwards the digital data supplied to it from the microprocessor 5 to the signal editing circuit 27 as corresponding analog signals via a control line 32. The digital data, or the corresponding analog signals, serve the purpose, for example, of setting the gain of the amplifier 27b, or completely inhibiting the amplifier 27b.

The digital data which are supplied to the microprocessor 5 via the line 29 are analyzed by the microprocessor 5 to determine whether indications of the occurrence of a natural heartbeat are contained in the electrical signal which corresponds to the activity of the heart 4. When the microprocessor 5 detects a natural heartbeat, or when it activates the stimulation pulse generator 20 via the line 22 to generate a stimulation pulse, the microprocessor 5 begins to operate as a counter, and thus begins to count a plurality of clock pulses derived from the oscillation of the crystal 14. This plurality corresponds to a time interval which is adjustable between an upper limit and a lower limit.

The time interval which is set defines the stimulation repetition rate with which the heart 4 is stimulated in the absence of natural heartbeats. If no data which the microprocessor 5 detects as a natural heartbeat proceed to the microprocessor 5 via the channel 17 during this time interval, the microprocessor 5 activates the stimulation pulse generator 20 via the line 22 after the expiration of the time interval. Following the generation of a stimulation pulse, the microprocessor 5 again begins to count a plurality of clock pulses corresponding to the time interval which defines the stimulation frequency. If, by contrast, the microprocessor 5 now detects a natural heartbeat during this interval, it aborts the counting process if a further time interval, known as the refractory time, has expired, and begins the counting process anew. The time interval which defines the stimulation repetition rate is adjustable between, for example, 400 and 2,000 ms. The refractory time is shorter than this time interval, and is adjustable to last between approximately 250 and 450 ms. The refractory time is in turn divided into an absolute refractory time, having a fixed duration of, usually, 125 ms, and a relative refractory time which includes the remaining portion of the total refractory time that has been set. The refractory time begins to run simultaneously with the time interval that defines the stimulation repetition rate, and is calculated by the microprocessor 5 during the course of the same counting process which serves for calculating the time interval that defines the stimulation repetition rate. The amplifier 27b of the signal editing circuit 2 in the channel 17 is completely inhibited during the absolute refractory time, which is achieved by means of an appropriate control signal from the microprocessor 5 to the amplifier 27b via the line 30, the digital-to-analog interface 31, and the control line 32. As a consequence of the complete inhibition of the amplifier 27b, no detection of any kind is possible with the microprocessor 5 for the duration of the absolute refractory time. After the expiration of the absolute fractory time, the microprocessor 5 re-activates the amplifier 27b, so that it is capable of detecting natural heartbeats. In contrast to a detection occurring after the expiration of the refractory time, if the microprocessor detects a natural heartbeat during the relative refractory time, it does not abort the counting process for calculating the time interval which defines the stimulation frequency, but instead continues counting and ceases counting with the activation of the stimulation pulse generator 20. After detection of a natural heartbeat, however, the microprocessor 5 again starts the full refractory time. This results in stimulation pulses being generated with the repetition rate defined by the time interval regardless of the occurrence of natural heartbeats, in case of high-frequency disturbances which can lead to incorrect detections. Even when the spontaneous heartbeat repetition rate is so high that the occurrence of natural heartbeats always occurs within the relative refractory time, the generation of stimulation pulses ensues with the stimulation repetition rate defined by the time interval which has been set, until the spontaneous heartbeat repetition rate has returned to a rate below the rate whose period corresponds to the refractory time which has been set. Termination of certain re-entry tachycardia is possible with this method.

The microprocessor 5 is connected to a telemetry circuit 34 via a line 33. A transmission/reception coil 35 is connected to the telemetry circuit 34. The pacemaker 1 is thus able to exchange data with an external programming device 36, having a keyboard 37 and a monitor 38. The programming device 36 is connected via a line 39 to a second telemetry circuit 40, having a transmission/reception coil 41. For data exchange between the implanted pacemaker 1 and the programming device 36, the transmission/reception coil 41 of the telemetry circuit 40 is positioned on the body surface of the patient in whom the pacemaker 1 has been implanted so that it is inductively coupled with the transmission/reception coil 35 of the pacemaker 1. The data contained in the ROM 6 and in the RAM 7 can thus be supplied to the programming device 36 for checking the data or for modifying the data. It is also possible to supply modified or additional data to the RAM 7 via the programming device 36.

Data is supplied to the microprocessor 5 via a channel 18 corresponding to the physical activity of the patient in whom the pacemaker 1 is implanted. This data is used, on the basis of the program stored in the ROM 6, to permit the microprocessor 5 to adapt the stimulation intensity, such as the time interval corresponding to the desired heartbeat rate, to the physical activity of the patient. For this purpose in the embodiment of FIG. 1, a piezoelectric pressure sensor 42 is attached to a wall of the housing 2 so as to be in indirect mechanical contact with the patient. During physical activity of the patient, mechanical oscillations in the body of the patient arise due to movement of the muscles and connecting tissue, which propagate in the body of the patient as pressure waves and are monitored by the piezoelectric sensor 42, which converts the pressure waves into electrical signals. These signals have an amplitude which increases with increasing physical activity. The signals proceed via a line 43 to a signal editing circuit 44, which contains a filter 44a and an amplifier 44b. The output signal of the signal editing circuit 44 proceeds via a line 45 to an analog-to-digital converter 46 which may be, for example, an 8-bit converter. The digital output signals of the converter 46 proceed via a line 47 to the microprocessor 5.

The microprocessor 5 is connected via a line 48 to a digital-to-analog interface 49, which forwards the digital data supplied to it by the microprocessor 5 to the signal editing circuit 44 as corresponding analog signals via a control line 50. The digital data and the analog signals corresponding thereto serve the purpose, for example, of setting the gain of the amplifier 44b or of varying the characteristic of the filter 44a. Dependent on the chronological curve of the signal derived from the piezoelectric sensor 42 (or the corresponding digital data) the microprocessor 5 varies the time interval which defines the stimulation rate such that, in a manner similar to that disclosed in U.S. Pat. No. 4,428,378, this time interval is shortened with increasing physical activity. This is accomplished between a lower limit (resting phase) and an upper limit (maximum heartbeat rate) which are selected corresponding to the requirements of the patient. Corresponding data are telemetrically entered in the RAM 7.

As noted above, the patient may assume a position while in a physical condition of rest, for example in the condition of sleep, such that pressure is exerted on the piezoelectric sensor 42 as a consequence of the weight of the patient's body, resulting in the time interval corresponding to the desired heartbeat rate being shortened, even though this is not required. To alleviate this situation, the program stored in the ROM 6 causes the microprocessor 5, possibly using data stored in the RAM 7, to continuously calculate a value F corresponding to the current heartbeat rate. The microprocessor 5 compares the value F to a corresponding threshold SWF 1. The microprocessor 5 also identifies that chronological duration T1 for which the value F downwardly transgresses the threshold SWF 1. The microprocessor 5 compares the chronological duration T1 to a minimum chronological duration SWT 1. If the microprocessor 5 determines that the minimum chronological duration SWT 1 was exceeded, it undertakes a reduction in the sensitivity E of the signal editing circuit 44 from a normal value N, i.e., it reduces the gain of the amplifier 44b so that a lower sensitivity value E1 is present instead of the normal value N.

To lower the sensitivity E by reducing the gain, the microprocessor 5 supplies the digital-to-analog interface 49 with corresponding digital data which are converted in the interface 49 into a suitable analog control signal which proceeds via the control line 50 to the signal editing circuit 44, and specifically to the amplifier 44b thereof. The sensitivity value E1 is selected such that only pressure influences on the piezoelectric sensor 42 having a strength corresponding to a noticeably increased physical activity of the patient can initiate the microprocessor 5 to shorten the time interval corresponding to the desired heartbeat rate.

If no such signals corresponding to increased physical activity of the patient occur during a second minimum chronological duration SWT 2, and when the value F corresponding to the heartbeat rate is below a second threshold SWF 2 (which is less than or equal to the threshold SWF 1) during the second minimum chronological duration SWT 2, another lowering of the sensitivity E to a second sensitivity value E2, lying below the sensitivity value E1, takes place. This is accomplished by operation of the device in the same manner set forth above in conjunction with the first reduction in sensitivity E.

Therefore, if the patient in whom the pacemaker is implanted remains in a rest condition or sleep condition during the second minimum chronological duration SWT 2, a further reduction in the sensitivity E ensues. The second sensitivity value E2 is selected such that a shortening of the time interval corresponding to the desired heartbeat rate can occur only if the patient begins a physical activity of considerable intensity.

If the sensitivity E of the amplifier 44b is reduced to the sensitivity value E1, and if the value F corresponding to the heartbeat rate exceeds the threshold SWF 1, the sensitivity E will be increased to its normal value N. Similarly, if the amplifier 44b is operating at the sensitivity value E2, and the value F exceeds the threshold SWF 2, the sensitivity E will be increased from E2 to E1.

In order to prevent small and brief-duration fluctuations of the heartbeat rate of the patient from causing modifications in the sensitivity E, the microprocessor 5 calculates the chronological average of the heartbeat rate over a plurality Z of device cycles. This average value is then used as the value F corresponding to heartbeat rate. The number of cycles Z is selected, taking the thresholds SWF 1 and SWF 2 into consideration, such that the averaging ensues over a time span which at least corresponds to the longer of the two minimum chronological durations SWT 1 and SWT 2. The calculation of the average preferably takes place by adding the time intervals which correspond to the desired heartbeat rate during Z cycles, and dividing the sum by Z.

It is also possible to calculate the actual heartbeat rate on the basis of the output stimulation pulses and on the basis of the detected natural heartbeats, as well as on the basis of the time intervals which have elapsed between these events.

The chronological durations T1 and T2, for which the thresholds SWF 1 and SWF 2 were downwardly transgressed, are calculated by the microprocessor 5 by the addition of the durations of the device cycles occurring after the downward transgression of the respective threshold SWF 1 or SWF 2.

Figure 2:
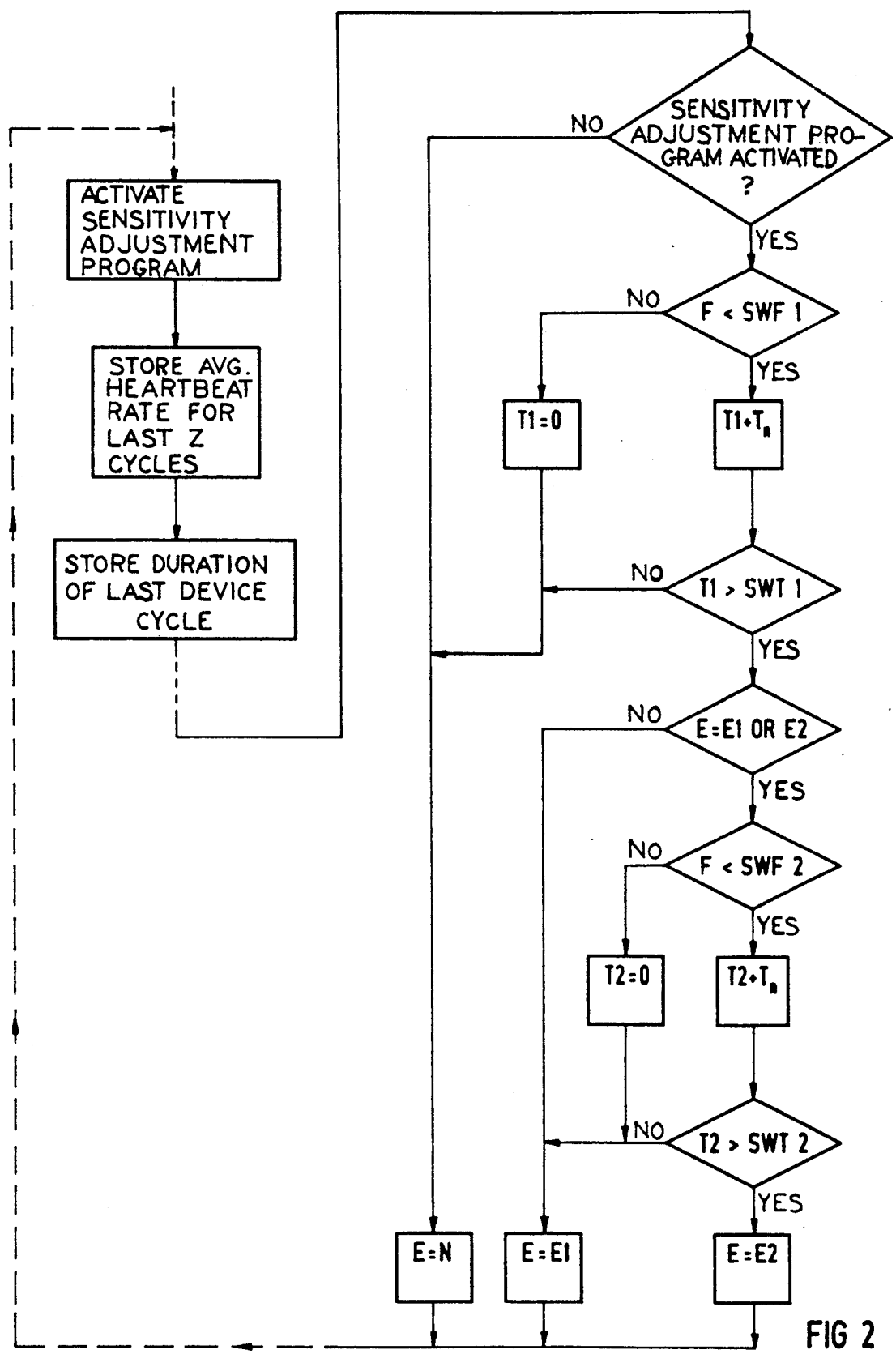
FIG. 2 is a flow chart for explaining the method of operation of the device of FIG. 1, in accordance with the principles of the present invention.

The above method of operation is shown in the form of a flow chart in FIG. 2, which is a schematic illustration of the program loop of the program stored in the ROM 6, to the extent necessary for explaining the method. This program includes a main program and a series of sub-programs, with that sub-program being shown in FIG. 2 which is used to set the sensitivity E for the signals from the piezoelectric sensor 42. Only a few steps are recited from the main program, which is shown as a dash-line loop, these steps being required for the execution of the illustrated sub-program.

After initiation, the main program performs one program loop per device cycle. Within the framework of the main program, there is the option of activating the sub-program for sensitivity adjustment. The steps of the method described above are executed only when this sub-program has been activated. Within the framework of the main program, additionally, the average of the heartbeat rate is formed for the last Z device cycles, and this average is stored and the duration of a preceding device cycle is also identified and stored. These operations could alternatively be a part of the sub-program for sensitivity adjustment, but are preferably executed within the framework of the main program because the calculated data are usable for purposes other than sensitivity adjustment.

A check to determine whether the sub-program for sensitivity adjustment has been activated is undertaken at a suitable location in the main program. If the response is affirmative, the content of a register, in which the time T1 which has elapsed since the downward transgression of the threshold SWF 1 is stored, is incremented by the duration $T_n$ of the preceding device cycle. This new, current chronological duration T1 is then compared to the minimum chronological duration SWT 1, and if SWT 1 has been exceeded, a check is undertaken to determine whether the current sensitivity E has one of the sensitivity values E1 or E2. If the sensitivity E has one of these values, a check is undertaken to determine whether the current average value F of the heartbeat rate also downwardly transgresses the second threshold SWF 2. If this is the case, the chronological duration T2 is also calculated in the manner set forth above in conjunction with the chronological duration T1. This chronological duration T2 is then compared to the minimum chronological duration SWT 2. If the chronological duration T2 falls below the minimum chronological duration SWT 2, the sensitivity E is set at the value E2, regardless of whether it previously had this value. Return to the main program then occurs.

If the sub-program for sensitivity adjustment is not activated, the sensitivity E is set to the normal value N before the return to the main program. This insures that possible adjustments of the sensitivity E which deviate from the normal value N after a deactivation of the sub-program are cancelled. If the check with respect to the threshold SWF 1 shows that it has not been downwardly transgressed, the chronological duration T1 is set to zero and the sensitivity E is set to the normal value N. This is required to assure that, following a preceding downward transgression of the threshold SWF 1, the chronological duration T1 calculated in this context is erased, and a lowering of the sensitivity which took place following a possible preceding upward transgression of the minimum chronological duration SWT 1 is cancelled. If the check with respect to the minimum chronological duration SWT 1 shows that the duration T1 has not yet exceeded the minimum chronological duration SWT 1, return to the main program takes place after the sensitivity E has been set to its normal value N. If no downward transgression of the threshold SWF 2 has occurred, the chronological duration T2 is set to zero, and the sensitivity E is set to the sensitivity value E1 in a corresponding manner. The sensitivity E is set to the value E1 only if an upward transgression of the minimum chronological duration SWT 2 has not occurred. This takes place before return to the main program.

The above steps are repeated for each device cycle. It is also possible, however, to continuously calculate the average F of the heartbeat rate and the durations T of the device cycles, and to undertake the check of the sensitivity setting only after the expiration of the defined time interval.

Instead of setting the sensitivity by influencing the gain of the amplifier 44b, it is possible to set the sensitivity by multiplying the values supplied to the microprocessor 5 by the digital-to-analog converter 46 by a suitable factor before those values are processed further. In this alternative, setting of the sensitivity is undertaken computationally.

In the above embodiment, a number of functions are undertaken by the appropriately programmed microprocessor 5. It will be understood by those skilled in the art, however, that separate electrical circuits may be provided for undertaking each of these functions.

If it is assumed that the normal value N of the sensitivity E corresponds to 100%, the sensitivity value E1 is preferably approximately 70%, and the sensitivity value E2 is preferably approximately 40%. Preferable values for the minimum chronological durations SWT 1 and SWT 2 are 10 minutes and 30 minutes, respectively. The thresholds SWF 1 and SWF 2 for the chronological average F of the heartbeat rate are dependent on the patient. Suitable values for use as guidelines are SWF 1=1.33 bps and SWF 2=1.17 bps.

Although the method and apparatus have been described above in the context of a heart pacemaker, it will be understood that the inventive concept disclosed herein can be used in other devices for stimulating physiological events.

Although further modifications and changes may be suggested by those skilled in the art, it is the intention of the inventors to embody within the patent warranted hereon all changes and modifications as reasonably and properly come within the scope of their contribution to the art.

We claim as our invention:

1. A medical device implantable in a patient, comprising:
    means for stimulating a physiological event in a patient at an adjustable stimulation intensity;
    means for automatically adapting adjustment of the stimulation intensity to the physical activity of said patient, including sensor means for generating a signal corresponding to said physical activity and means for setting a sensitivity of said stimulation intensity to said signal, said sensitivity normally having a normal value;
    means for calculating a value corresponding to said stimulation intensity;
    means for comparing said value to a threshold;
    means for calculating a duration during which said value is below said threshold;
    means for comparing said duration to a minimum duration; and
    means for lowering said sensitivity to a sensitivity value less than said normal value if said duration exceeds said minimum duration.

2. A medical device as claimed in claim 1 further comprising:
    means for comparing said value corresponding to said stimulation intensity to a further threshold which is less than or equal to said threshold;
    means for calculating a further duration during which said value corresponding to said stimulation intensity is below said further threshold;
    means for comparing said further duration to a further minimum duration; and
    means for lowering said sensitivity to a further sensitivity value, less than said sensitivity value, if said further duration exceeds said further minimum duration.

3. A medical device as claimed in claim 1 wherein said means for calculating a value corresponding to said stimulation intensity is a means for calculating a value corresponding to the chronological average of said stimulation intensity over a selected time.

4. A medical device as claimed in claim 1 wherein said sensor means is a piezoelectric pressure sensor adapted to be disposed in mechanical contact with the body of said patient.

5. A medical device as claimed in claim 1 wherein said device is a heart pacemaker, and wherein said means for stimulating a physiological event comprises means for stimulating heart activity in said patient at an adjustable stimulation rate.

6. A method for operating a medical device implantable in a patient, comprising the steps of:
    stimulating a physiological event in a patient at an adjustable stimulation intensity;
    automatically adapting adjustment of the stimulation intensity to the physical activity of said patient, including sensing the physical activity of said patient and generating an electrical signal corresponding thereto;
    setting a sensitivity of said stimulation intensity to said signal, said sensitivity normally being set at a normal value;
    calculating a value corresponding to said stimulation intensity;
    comparing said value to a threshold;
    calculating a duration during which said value is below said threshold;
    comparing said duration to a minimum duration; and
    lowering said sensitivity to a sensitivity value less than said normal value if said duration exceeds said minimum duration.

7. A method as claimed in claim 6 comprising the additional steps of:

comparing said value corresponding to said stimulation intensity to a further threshold;
calculating a further duration during which said value corresponding to said stimulation intensity is below said further threshold;
comparing said further duration to a further minimum duration; and
lowering said sensitivity to a further sensitivity value less than said sensitivity value if said further duration exceeds said further minimum duration.

8. A method as claimed in claim 6 wherein the step of calculating a value corresponding to said stimulation intensity is further defined by calculating a value corresponding to said stimulation intensity which is an average of said stimulation intensity over a selected time.

9. A method as claimed in claim 6 wherein the step of stimulating a physiological event in a patient is further defined by stimulating heart activity in said patient at an adjustable stimulation rate.

* * * * *